United States Patent
Twomey (10) Patent No.: US 9,808,259 B2
(45) Date of Patent: Nov. 7, 2017

(54) CLIP-OVER DISPOSABLE ASSEMBLY FOR USE WITH HEMOSTAT-STYLE SURGICAL INSTRUMENT AND METHODS OF MANUFACTURING SAME

(71) Applicant: COVIDIEN LP, Mansfield, MA (US)

(72) Inventor: John R. Twomey, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/804,790

(22) Filed: Jul. 21, 2015

(65) Prior Publication Data
US 2015/0327912 A1   Nov. 19, 2015

Related U.S. Application Data

(63) Continuation of application No. 14/546,152, filed on Nov. 18, 2014, now Pat. No. 9,113,891, which is a (Continued)

(51) Int. Cl.
*A61B 18/18* (2006.01)
*A61B 17/128* (2006.01)
(Continued)

(52) U.S. Cl.
CPC ............ *A61B 17/128* (2013.01); *A61B 17/28* (2013.01); *A61B 17/2812* (2013.01);
(Continued)

(58) Field of Classification Search
CPC ... A61B 17/128; A61B 17/28; A61B 17/2812; A61B 18/1442; A61B 2017/0023;
(Continued)

(56) References Cited

U.S. PATENT DOCUMENTS

D223,367 S   4/1972   Kountz
D263,020 S   2/1982   Rau, III
(Continued)

FOREIGN PATENT DOCUMENTS

CN   1103807 A   6/1995
DE   390937 C    3/1924
(Continued)

OTHER PUBLICATIONS

Cosman et al., "Radiofrequency Lesion Generation and its Effect on Tissue Impedence", Applied Neurophysiology, 51:230-242, 1988.
(Continued)

*Primary Examiner* — Michael Peffley
*Assistant Examiner* — Amanda Zink (57) ABSTRACT

A clip-over disposable assembly includes a switch assembly and a disposable body. The disposable body includes a first disposable member, a second disposable member including first and second wall portions, and a third disposable member. The first wall portion defines a first aperture therethrough and a first cavity configured to receive therein a first portion of the switch assembly. The third disposable member includes a third wall portion, wherein a body of the second disposable member and the third wall portion define an opening configured to allow a shaft of a hemostat-style surgical instrument to pass therethrough. The second wall portion and the third wall portion cooperatively define a chamber in communication with the opening and configured to receive therein at least a portion of the shaft of the hemostat-style surgical instrument, wherein the at least a portion of the shaft is received in the chamber from an off-axis position.

10 Claims, 5 Drawing Sheets

Related U.S. Application Data continuation of application No. 13/183,856, filed on Jul. 15, 2011, now Pat. No. 8,888,771.

(51) Int. Cl.
  *A61B 17/28* (2006.01)
  *A61B 18/14* (2006.01)
  *A61B 18/00* (2006.01)
  *A61B 17/00* (2006.01)

(52) U.S. Cl.
  CPC .. *A61B 18/1442* (2013.01); *A61B 2017/0023* (2013.01); *A61B 2018/00077* (2013.01); *A61B 2018/00928* (2013.01); *A61B 2018/1495* (2013.01); *Y10T 29/49826* (2015.01)

(58) Field of Classification Search
  CPC ........... A61B 2018/00077; A61B 2018/00928; A61B 2018/1495
  See application file for complete search history.

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,552,143 A | 11/1985 | Lottick | |
| D295,893 S | 5/1988 | Sharkany et al. | |
| D295,894 S | 5/1988 | Sharkany et al. | |
| D354,218 S | 1/1995 | Van de Peer | |
| D424,693 S | 5/2000 | Pruter | |
| D424,694 S | 5/2000 | Tetzlaff et al. | |
| D425,201 S | 5/2000 | Tetzlaff et al. | |
| 6,277,117 B1 * | 8/2001 | Tetzlaff .............. A61B 18/1445 606/48 |
| D449,886 S | 10/2001 | Tetzlaff et al. | |
| 6,325,795 B1 | 12/2001 | Lindemann et al. | |
| 6,334,861 B1 | 1/2002 | Chandler et al. | |
| D457,958 S | 5/2002 | Dycus et al. | |
| D457,959 S | 5/2002 | Tetzlaff et al. | |
| D487,039 S | 2/2004 | Webster et al. | |
| 6,796,981 B2 | 9/2004 | Wham et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| 7,131,970 B2 | 11/2006 | Moses et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,252,667 B2 | 8/2007 | Moses et al. | |
| D564,662 S | 3/2008 | Moses et al. | |
| D576,932 S | 9/2008 | Strehler | |
| 7,442,193 B2 | 10/2008 | Shields et al. | |
| 7,491,202 B2 | 2/2009 | Odom et al. | |
| 7,510,556 B2 | 3/2009 | Nguyen et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,846,161 B2 | 12/2010 | Dumbauld et al. | |
| D634,010 S | 3/2011 | DeCarlo | |
| 7,955,332 B2 | 6/2011 | Arts et al. | |
| 8,317,703 B2 | 11/2012 | Brannan | |
| 8,361,062 B2 | 1/2013 | Bonn | |
| 8,376,948 B2 | 2/2013 | Brannan | |
| 8,398,626 B2 | 3/2013 | Buysse et al. | |
| 8,643,561 B2 | 2/2014 | Prakash et al. | |
| 8,690,866 B2 | 4/2014 | Brannan | |
| 8,696,667 B2 | 4/2014 | Guerra et al. | |
| 8,745,846 B2 | 6/2014 | Behnke, II et al. | |
| 8,745,854 B2 | 6/2014 | Bonn | |
| 8,747,402 B2 | 6/2014 | Mahajan et al. | |
| 8,832,927 B2 | 9/2014 | Smith et al. | |
| 8,870,860 B2 | 10/2014 | Lee et al. | |
| 8,888,771 B2 | 11/2014 | Twomey | |
| 8,932,281 B2 | 1/2015 | Brannan | |
| 9,113,891 B2 | 8/2015 | Twomey | |
| 2002/0107517 A1 | 8/2002 | Witt et al. | |
| 2005/0107785 A1 | 5/2005 | Dycus et al. | |
| 2005/0113827 A1 | 5/2005 | Dumbauld et al. | |
| 2005/0113828 A1 | 5/2005 | Shields et al. | |
| 2005/0154387 A1 | 7/2005 | Moses et al. | |
| 2006/0167452 A1 | 7/2006 | Moses et al. | |
| 2007/0078458 A1 | 4/2007 | Dumbauld et al. | |
| 2007/0088356 A1 | 4/2007 | Moses et al. | |
| 2007/0106295 A1 | 5/2007 | Garrison et al. | |
| 2007/0106297 A1 | 5/2007 | Dumbauld et al. | |
| 2007/0118111 A1 | 5/2007 | Weinberg | |
| 2007/0149962 A1 * | 6/2007 | Wittenberger ......... A61B 18/02 606/23 |
| 2007/0260238 A1 | 11/2007 | Guerra | |
| 2007/0260241 A1 | 11/2007 | Dalla Betta et al. | |
| 2012/0041433 A1 | 2/2012 | Prakash et al. | |
| 2012/0123403 A1 | 5/2012 | Brannan | |
| 2012/0161786 A1 | 6/2012 | Brannan | |
| 2012/0165806 A1 | 6/2012 | Brannan | |
| 2012/0172860 A1 | 7/2012 | Brannan | |
| 2012/0172861 A1 | 7/2012 | Brannan | |
| 2012/0172862 A1 | 7/2012 | Brannan | |
| 2012/0203217 A1 | 8/2012 | Brannan | |
| 2012/0203218 A1 | 8/2012 | Bonn | |
| 2012/0232544 A1 | 9/2012 | Willyard et al. | |
| 2012/0232549 A1 | 9/2012 | Willyard et al. | |
| 2012/0239024 A1 | 9/2012 | Ladtkow et al. | |
| 2012/0259324 A1 | 10/2012 | Brannan | |
| 2012/0259329 A1 | 10/2012 | DeCarlo | |
| 2012/0303018 A1 | 11/2012 | Ladtkow et al. | |
| 2012/0310228 A1 | 12/2012 | Bonn et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0178841 A1 | 7/2013 | Reid, Jr. | |
| 2013/0178842 A1 | 7/2013 | Reid, Jr. | |
| 2013/0178843 A1 | 7/2013 | Lee et al. | |
| 2013/0178844 A1 | 7/2013 | Lee et al. | |
| 2013/0190749 A1 | 7/2013 | Willyard et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |

(56) References Cited

FOREIGN PATENT DOCUMENTS

| | | |
|---|---|---|
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| EP | 1609430 A1 | 12/2005 |
| EP | 1645240 A2 | 4/2006 |
| EP | 1810628 A1 | 7/2007 |
| EP | 1852079 A1 | 11/2007 |
| EP | 2301468 A1 | 3/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 00/24330 | 5/2000 |
| WO | 02/080784 | 10/2002 |
| WO | 02/080785 | 10/2002 |
| WO | 2010/035831 A1 | 4/2010 |

OTHER PUBLICATIONS

Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non.cndot.LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas. "Compact Directional Microwave Antenna for Localized Heating," NASA Tech Briefs, Mar. 2008.

(56) References Cited

OTHER PUBLICATIONS

M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2003); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.

(56) References Cited

OTHER PUBLICATIONS

European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report for European Application No. 12176517.6 dated Sep. 28, 2012.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.

(56) References Cited

OTHER PUBLICATIONS

Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94ln Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

* cited by examiner

CLIP-OVER DISPOSABLE ASSEMBLY FOR USE WITH HEMOSTAT-STYLE SURGICAL INSTRUMENT AND METHODS OF MANUFACTURING SAME

CROSS-REFERENCE TO RELATED APPLICATIONS

The present application is a continuation application of U.S. patent application Ser. No. 14/546,152 filed on Nov. 18, 2014, now U.S. Pat. No. 9,113,891, which is a continuation application of U.S. patent application Ser. No. 13/183,856 filed on Jul. 15, 2011, now U.S. Pat. No. 8,888,771, the entire contents of which are incorporated herein by reference.

BACKGROUND

1. Technical Field

The present disclosure relates to electrosurgical instruments and, more particularly, to a clip-over disposable assembly for use with a hemostat-style surgical instrument, such as a bipolar forceps, and methods of manufacturing a clip-over disposable assembly.

2. Discussion of Related Art

Electrosurgery involves the application of thermal and/or electrical energy, such as radiofrequency energy, to coagulate, cauterize, cut and/or seal tissue. Electrosurgical devices have been developed for a variety of uses and applications.

Generally, the electrical configuration of electrosurgical devices can be categorized in two classifications: 1) monopolar electrosurgical devices; and 2) bipolar electrosurgical devices. Monopolar electrosurgical devices utilize one electrode associated with a cutting and/or cauterizing instrument and a remote return electrode, usually adhered externally to the patient. Bipolar devices utilize two generally opposing electrodes of a tissue treating portion (e.g., end effector) of an instrument, wherein the electrical current is generally limited to tissue disposed between the two electrodes.

A hemostat or forceps is a surgical device configured to use mechanical action between its jaws to constrict vessels and is commonly used in open surgical procedures to grasp, dissect and/or clamp tissue. Some hemostat-style surgical instruments, such as monopolar electrosurgical forceps and bipolar electrosurgical forceps, utilize both mechanical clamping action and electrosurgical energy to effect hemostasis by heating tissue and blood vessels to coagulate, cauterize, cut and/or seal tissue. By utilizing an electrosurgical forceps, a surgeon can cauterize, coagulate, desiccate and/or cut tissue and/or simply reduce or slow bleeding, by controlling the intensity, frequency and duration of the electrosurgical energy applied to tissue.

Monopolar electrosurgical forceps utilize one active electrode associated with the clamping end effector to deliver energy from an electrosurgical generator to tissue and a remote patient return electrode, usually positioned on the patient's thigh or back, to complete the electrical circuit between the electrosurgical generator and the patient. When electrosurgical energy is applied, the energy travels from the active electrode, to the surgical site, through the patient and to the return electrode.

Bipolar electrosurgical forceps utilize two electrodes, usually disposed on the inner facing or opposing surfaces of end effectors, which are, in turn, electrically coupled to an electrosurgical generator. Each electrode is charged to a different electric potential. When the end effectors are utilized to clamp or grasp tissue therebetween, the electrical energy can be selectively transferred from one electrode, through the intervening tissue to the other electrode.

In the use of many prior art electrosurgical instruments, cleaning and sterilizing is often impractical as electrodes and/or insulation can be damaged. It is known that electrically insulative materials, such as plastics, can be damaged or compromised by repeated sterilization cycles. To prolong the useful life of electrosurgical instruments, portions of an instrument may be disposable to allow the instrument to be used and sterilized a greater number of times.

SUMMARY

The present disclosure relates to a clip-over disposable assembly suitable for use with a hemostat-style surgical instrument. The clip-over disposable assembly includes a switch assembly and a disposable body configured for side-mounting onto the hemostat-style surgical instrument. The disposable body includes a first disposable member, a second disposable member and a third disposable member. The first disposable member includes first and second wall portions. The first wall portion defines a first aperture therethrough and a first cavity associated with the first aperture. The first cavity is configured to receive therein a first portion of the switch assembly. The second disposable member includes a body defining a second aperture therethrough and a second cavity associated with the second aperture. The second cavity is configured to receive therein a second portion of the switch assembly. The third disposable member includes a third wall portion, wherein the body of the second disposable member and the third wall portion define an opening configured to allow the shaft of the hemostat-style surgical instrument to pass therethrough, and wherein the second wall portion of first disposable member and the third wall portion cooperatively define a chamber in communication with the opening. The chamber is configured to receive therein at least a portion of the shaft of the hemostat-style surgical instrument, wherein the at least a portion of the shaft is received in the chamber from an off-axis position.

The present disclosure also relates to an electrosurgical instrument including a hemostat-style surgical instrument and a clip-over disposable assembly adapted to be releaseably attachable to the hemostat-style surgical instrument The clip-over disposable assembly includes a switch assembly, a first disposable member, a second disposable member, and a third disposable member. The first disposable member includes first and second wall portions. The first wall portion defines a first aperture therethrough and a first cavity associated with the first aperture. The first cavity is configured to receive therein a first portion of the switch assembly. The second disposable member includes a body defining a second aperture therethrough and a second cavity associated with the second aperture. The second cavity is configured to receive therein a second portion of the switch assembly. The third disposable member includes a third wall portion, wherein the third wall portion and the second wall portion cooperatively define a chamber configured to receive therein at least a portion of a shaft of the hemostat-style surgical instrument.

The present disclosure also relates to a method of manufacturing a clip-over disposable assembly including the initial steps of providing a switch assembly, and providing first and second disposable members configured to form an internal chamber when the first and second disposable members are coupled together. The chamber is configured to accommodate at least a portion of the switch assembly therein. The method also includes the steps of coupling the second disposable member to the first disposable member, wherein a first portion of a user-actuatable button of the switch assembly is disposed in association with an outer peripheral surface of the first disposable member and a second portion of the user-actuatable button is disposed in association with an outer peripheral surface the second disposable member, and providing a third disposable member including a wall portion configured to form a chamber when the first and third disposable members are coupled together, wherein the chamber configured to receive therein at least a portion of a shaft of a hemostat-style surgical instrument, and coupling the third disposable member to the first disposable member.

The present disclosure also relates to a method of manufacturing a clip-over disposable assembly including the initial steps of providing a switch assembly, providing a first disposable member, and providing a second disposable member. The first disposable member includes first and second wall portions. The first wall portion defines a first aperture therethrough and a first cavity associated with the first aperture. The first cavity is configured to receive therein a first portion of the switch assembly. The second disposable member includes a body defining a second aperture therethrough and a second cavity associated with the second aperture. The second cavity is configured to receive therein a second portion of the switch assembly. The method also includes the steps of positioning the first portion of the switch assembly into the first cavity, positioning the second portion of the switch assembly into the second cavity, coupling the second disposable member to the first disposable member, providing a third disposable member including a third wall portion, and coupling the third disposable member to the first disposable member, wherein the third wall portion and the second wall portion cooperatively define a chamber configured to receive therein at least a portion of a shaft of a hemostat-style surgical instrument.

BRIEF DESCRIPTION OF THE DRAWINGS

Objects and features of the presently-disclosed clip-over disposable assembly for use with a hemostat-style surgical instrument and methods of manufacturing a clip-over disposable assembly will become apparent to those of ordinary skill in the art when descriptions of various embodiments thereof are read with reference to the accompanying drawings, of which.

DETAILED DESCRIPTION

Hereinafter, embodiments of the presently-disclosed clip-over disposable assembly for use with a hemostat-style surgical instrument and methods of manufacturing a clip-over disposable assembly are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

As it is used in this description, "transmission line" generally refers to any transmission medium that can be used for the propagation of signals from one point to another.

Various embodiments of the present disclosure provide electrosurgical instruments suitable for sealing, cauterizing, coagulating/desiccating and/or cutting vessels and vascular tissue. Embodiments may be implemented using electromagnetic radiation at microwave frequencies or at other frequencies.

Various embodiments of the presently-disclosed electrosurgical instrument including a hemostat-style surgical instrument and a clip-over disposable assembly are suitable for use with open and/or laparoscopic surgical procedures. Although the following description describes the use of a bipolar forceps, the teachings of the present disclosure may also apply to a monopolar forceps, or other suitable type of hemostat-style surgical instrument.

Figure 1:
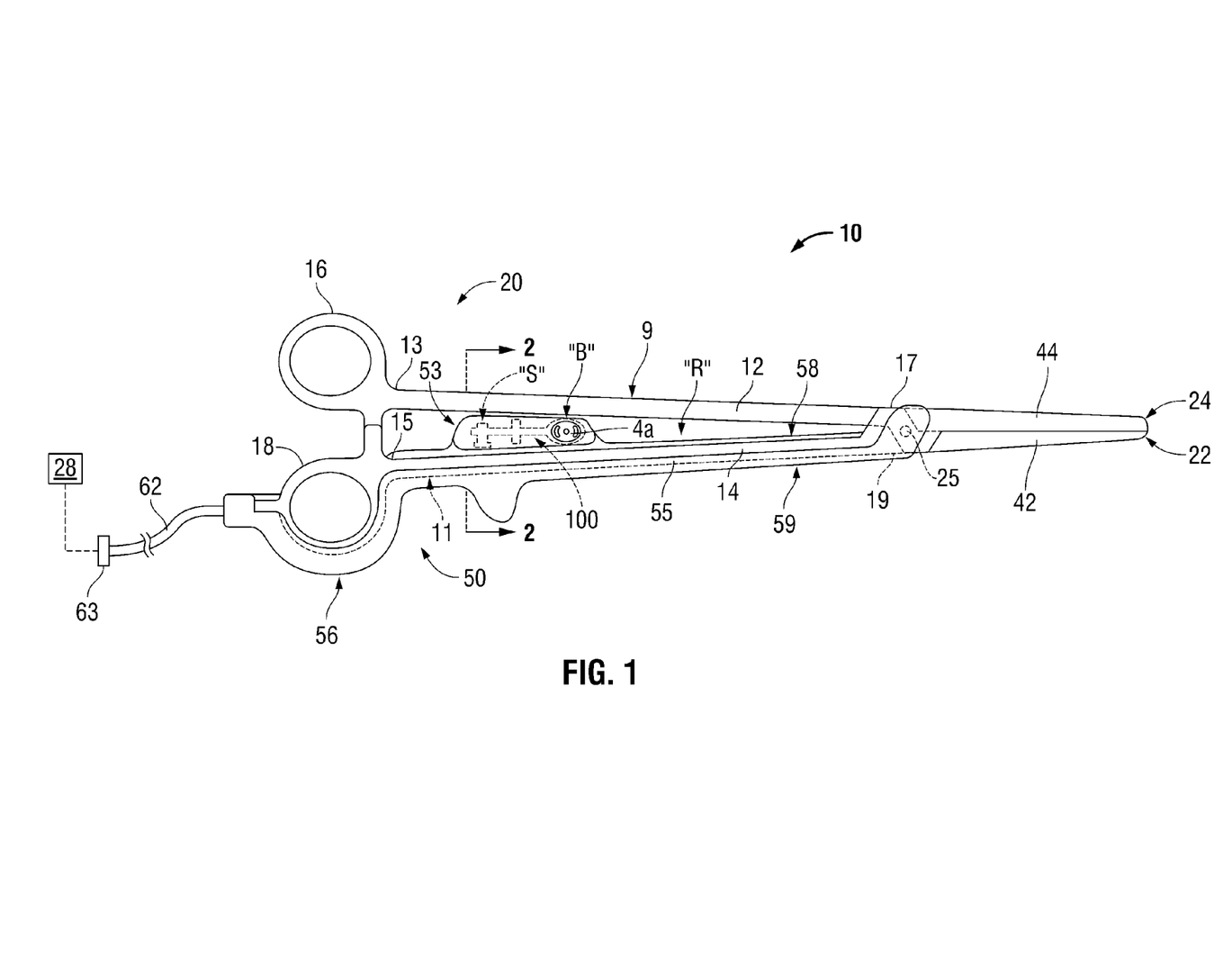
FIG. 1 is a side view of a bipolar forceps in accordance with an embodiment of the present disclosure.

FIG. 1 shows a bipolar forceps 10 according to an embodiment of the present disclosure that includes a mechanical forceps 20 and a clip-over assembly 50. Clip-over assembly 50 is configured to accommodate a switch assembly 100, partly shown by phantom lines in FIG. 1. An embodiment of a switch assembly, such as the switch assembly 100 of FIG. 1, in accordance with the present disclosure, is shown in more detail in FIGS. 3 and 4. It will be understood, however, that other switch assembly embodiments may also be used. Clip-over assembly 50, which is described in more detail later in this disclosure, is generally configured to be releaseably attachable to the mechanical forceps 20.

Mechanical forceps 20 includes first and second members 9 and 11. First and second members 9 and 11 each include an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18, respectively, attached thereto to allow a user to effect movement of at least one of the shaft portions 12 and 14 relative to one another. Extending from the distal end 17 and 19 of each shaft portion 12 and 14 are end effectors 22 and 24, respectively. End effectors 22 and 24 are movable relative to one another in response to movement of the handle members 16 and 18.

In some embodiments, as shown in FIG. 1, shaft portions 12 and 14 are affixed to one another at a point proximate the end effectors 22 and 24 about a pivot 25 such that movement of the handle members 16 and 18 impart movement of the end effectors 22 and 24 from an open configuration, wherein the end effectors 22 and 24 are disposed in spaced relation relative to one another, to a clamping or closed configuration, wherein the end effectors 22 and 24 cooperate to grasp tissue therebetween. In alternative embodiments not shown, the forceps 10 can be designed such that movement of one or both of the handle members 16 and 18 will only cause one of the end effectors, e.g., 22, to move with respect to the other end effector, e.g., 24.

End effector 24 generally includes an upper or first jaw member 44. End effector 22 generally includes a second or lower jaw member 42. In some embodiments, shaft members 12 and 14 of the mechanical forceps 20 may be designed to transmit a particular desired force to opposing inner-facing surfaces of the jaw members 42 and 44.

Examples of shaft member and end effector embodiments are disclosed in commonly assigned U.S. Pat. No. 6,277,117 entitled "OPEN VESSEL SEALING FORCEPS WITH DISPOSABLE ELECTRODES", commonly assigned U.S. Pat. No. 6,796,981 entitled "VESSEL SEALING SYSTEM", commonly assigned U.S. Pat. No. 7,510,556 entitled "VESSEL SEALING INSTRUMENT", and commonly assigned U.S. patent application Ser. No. 11/232,174 filed on Sep. 21, 2005, entitled "MECHANISM FOR DIVIDING TISSUE IN A HEMOSTAT-STYLE INSTRUMENT".

Forceps 10 includes a cable assembly 62 configured to operably couple the forceps 10 to an electrosurgical power generating source 28, e.g., a microwave or RF electrosurgical generator. Cable assembly 62 may be formed from a suitable flexible, semi-rigid or rigid cable, and may connect directly to the electrosurgical power generating source 28. In some embodiments, the cable assembly 62 connects the forceps 10 to a connector 63, which further operably connects the instrument 10 to the electrosurgical power generating source 28. Cable assembly 62 may be internally divided into a plurality of conductors (e.g., 61a, 61b, 61c shown in FIG. 2) configured to transmit electrosurgical energy through respective feed paths to the end effectors 22 and 24 and/or transmitting electrical signals to control delivery of electrosurgical energy and/or feedback signals to control the electrosurgical power generating source 28.

Electrosurgical power generating source 28 may include any energy source, e.g., electrosurgical generator, suitable for use with electrosurgical devices, and may be configured to provide ultrasound, radiofrequency (RF), microwaves, laser energy and/or various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Cable assembly 62 may additionally, or alternatively, provide a conduit (not shown) configured to provide coolant fluid from a coolant source (not shown) to one or more components of the forceps 10. Forceps 10 may alternatively be configured as a wireless device and/or battery powered.

Figure 2:
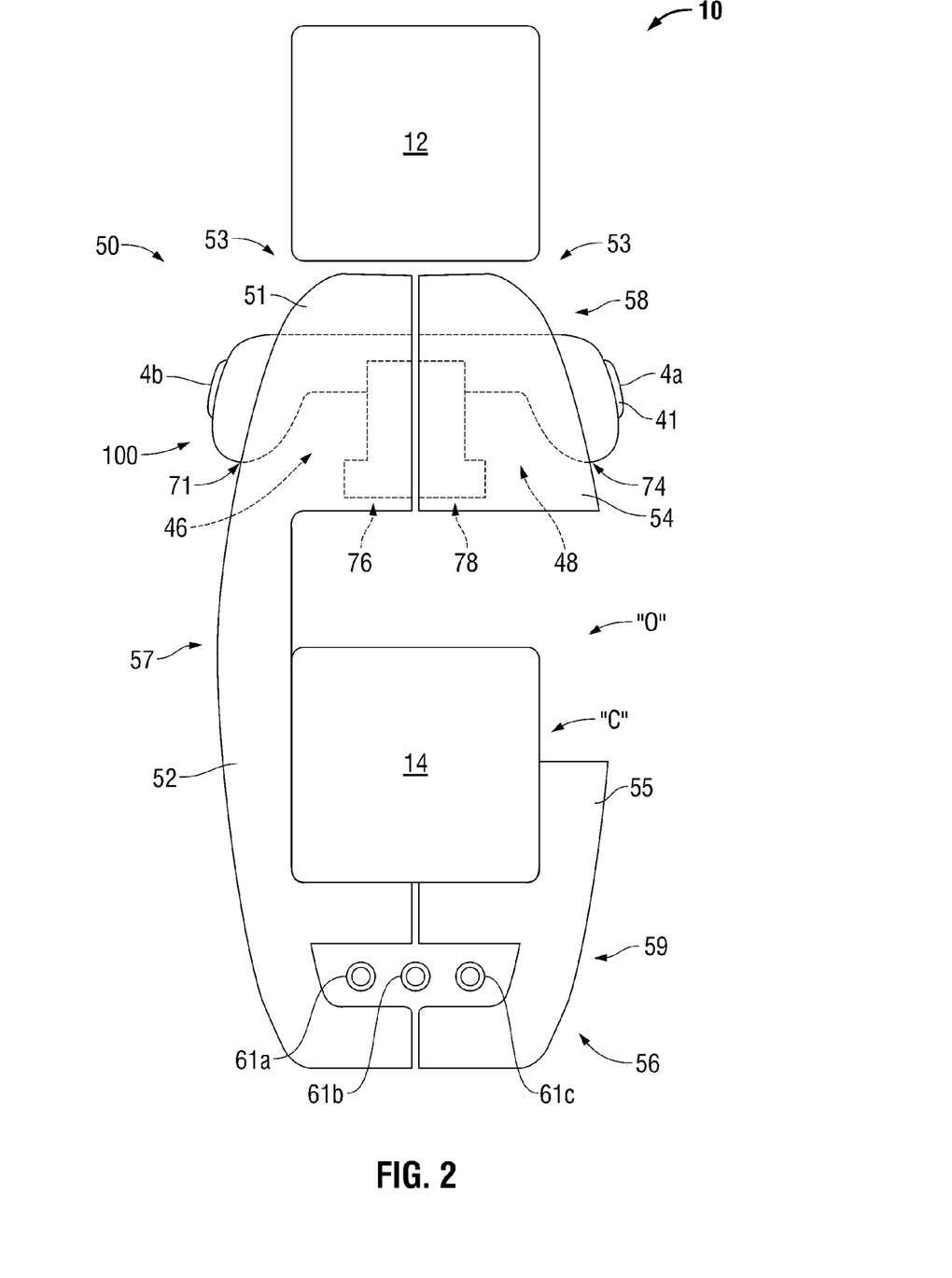
FIG. 2 is an enlarged, cross-sectional view taken along line 2-2 of FIG. 1.

As shown in FIGS. 1 and 2, clip-over assembly 50 is designed to work in combination with the mechanical forceps 20. Clip-over assembly 50 is designed to clip around the mechanical forceps 20 from the side and includes a disposable body 56 configured to releaseably engage one of the shaft members, e.g., 14, of the mechanical forceps 20. In some embodiments, as shown in FIG. 2, disposable body 56 includes a first disposable member 57, a second disposable member 58 and a third disposable member 59, wherein the second disposable member 58 is coupled to the first disposable member 57 to cooperatively define a tab portion 53, and the third disposable member 59 is coupled to the first disposable member 57 to cooperatively define a chamber "C", wherein the chamber "C" is disposed in communication with an opening "O" defined by the second disposable member 58 and the third disposable member 59. Tab portion 53 is configured to accommodate the switch assembly 100 therein and suitably shaped to fit within the region "R" (FIG. 1) defined between the opposing shaft portions 12 and 14.

First disposable member 57, the second disposable member 58 and/or the third disposable member 59 may include a plurality of mechanical interfaces disposed at various positions along their respective interiors to effect mechanical engagement with one another. In some embodiments, either male or female mechanical interfaces or a combination of mechanical interfaces may be disposed within the second disposable member 58 and/or the third disposable member 59 with mating mechanical interfaces disposed on or within the first disposable member 57. First disposable member 57, second disposable member 58 and the third disposable member 59 may be assembled together with the aid of alignment pins, detents, snap-like interfaces, tongue and groove interfaces, locking tabs, adhesive ports, etc., utilized either alone or in combination for assembly purposes. Any suitable joining method may be used to attach (or clip, connect, couple, fasten, secure, etc.) the second and third disposable members 58, 59 to the first disposable member 57. In alternative embodiments not shown, the first disposable member 57 and the third disposable member 59 are integrally formed as a single unitary body by a suitable molding process, such as injection molding.

First disposable member 57, the second disposable member 58, and the third disposable member 59 may be formed in whole or in part of any suitable electrically non-conductive material, e.g., a suitable polymeric or ceramic material. In some embodiments, the first disposable member 57, the second disposable member 58 and/or the third disposable member 59 are formed at least in part from a rigid material, such as polyamide or other plastic, or a composite material having low electrical conductivity, e.g., glass-reinforced polymers. In some embodiments, the first disposable member 57, the second disposable member 58 and/or the third disposable member 59, or portions thereof, may be formed from metal, thermoplastic, e.g., polycarbonate, composites, e.g., plastic-metal or ceramic-metal composites, or other materials.

As shown in FIG. 2, first disposable member 57 includes a first wall portion 51 and a second wall portion 52. First wall portion 51 defines a first aperture 71 therethrough and a first cavity 76 associated with the first aperture 71. First cavity 76 is configured to receive therein a first portion (e.g., 46 shown in FIGS. 2 and 4) of the switch assembly 100. Second disposable member 58 includes a body 54 defining a second aperture 74 therethrough and a second cavity 78 associated with the second aperture 74. Second cavity 78 is configured to receive therein a second portion (e.g., 48 shown in FIGS. 2 and 4) of the switch assembly 100. Third disposable member 59 includes a third wall portion 55. Third wall portion 55 of the third disposable member 59 and the body 54 of the second disposable member 58 are adapted to cooperatively define an opening "O" configured to allow one of the shaft members, e.g., 14, of the mechanical forceps 20 to pass therethrough. Third wall portion 55 of the third disposable member 59 and the second wall portion 52 of first disposable member 57 are adapted to cooperatively define a chamber "C" configured to receive therein at least a portion of one of the shaft members, e.g., 14, of the mechanical forceps 20, wherein chamber "C" is disposed in communication with the opening "O". In some embodiments, at least a portion of the cable assembly 62 is housed within the clip-over assembly 50.

Although the clip-over assembly 50 is adapted to releaseably-engage the mechanical forceps 20, bipolar forceps 10 can be manufactured wherein the clip-over assembly 50 may be permanently or semi-permanently affixed to the mechanical forceps 20 by any suitable process including without limitation mechanical fasteners, grooves, flanges, adhesive bonding, welding processes, e.g., laser welding, mechanical interlock, snaps, bent tabs, or other suitable joining method may be used to attach (or clip, connect, couple, fasten, secure, etc.) the clip-over assembly 50 to the mechanical forceps 20.

As cooperatively shown in FIGS. 1 and 2, switch assembly 100 includes a user-actuatable button "B" including two user-accessible contact areas 4a and 4b (e.g., disposed on opposite sides of the mechanical forceps 20) configured to allow finger actuation of a switch "S". Switch "S" may include any suitable switch, e.g., a joystick switch or other control mechanism, and may be disposed in operative communication with a source of electrosurgical energy 28 and/or a processor unit (not shown) configured to control delivery of electrosurgical energy to the forceps 10.

Figure 3:
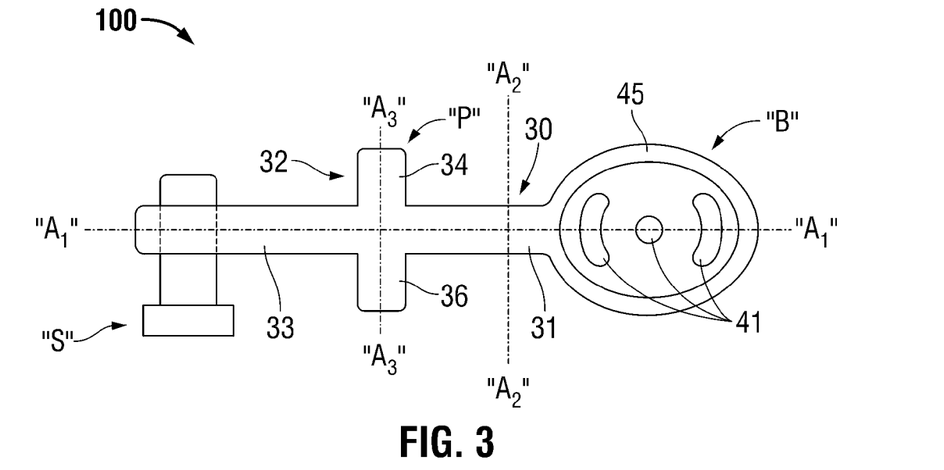
FIG. 3 is a top view of a switch assembly in accordance with an embodiment of the present disclosure.
Figure 4:
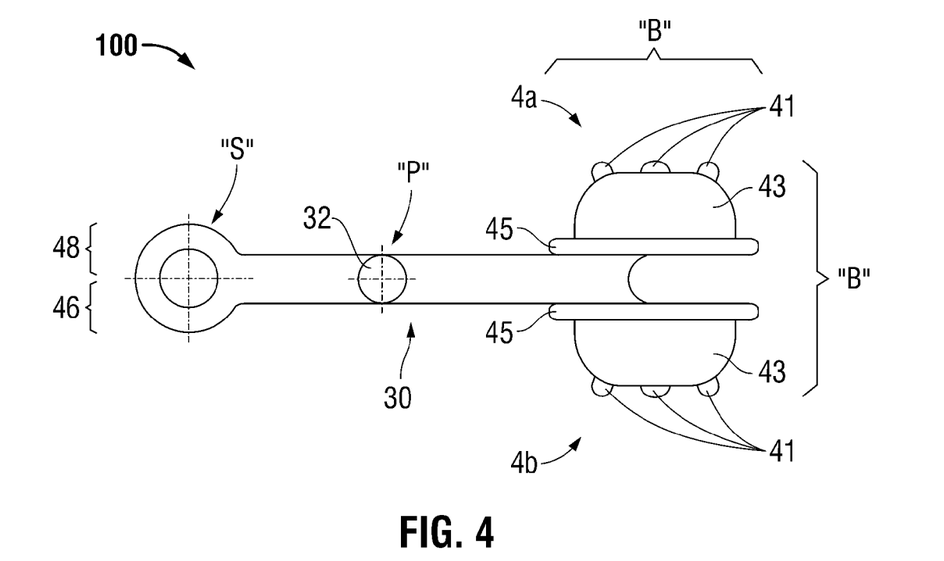
FIG. 4 is a side view of the switch assembly of FIG. 3 in accordance with an embodiment of the present disclosure.

In some embodiments, as shown in FIGS. 3 and 4, contact areas 4a and 4b may include one or more features, e.g., protrusions or contact bumps 41 raised on the face of the contact areas 4a and 4b, to increase operability and/or enhance ease-of-use of the button "B". The shape, size and spacing of individual contact bumps 41 may be varied from the configuration depicted in FIGS. 3 and 4.

As shown in FIGS. 3 and 4, switch assembly 100 includes a connector member 30 adapted to operably couple the button "B" and the switch "S". Connector member 30 includes a post member "P" operably associated between the button "B" and the switch "S". As shown in FIG. 3, post member "P" includes a post body 32 including two prong-like portions 34 and 36 extending outwardly from the connector member 30. Connector member 30 includes a first connector portion 31 disposed to place the contact areas 4a and 4b in operative association with the post body 32, and may include a second connector portion 33 disposed to place the post body 32 in operative association with the switch "S". In some embodiments, the post body 32 bisects or otherwise divides the connector member 30 into the first connector portion 31 and the second connector portion 33.

In some embodiments, button "B" includes a flange 45 disposed in association with the first and second contact areas 4a and 4b. Flange 45 is configured to facilitate positioning of the button "B", and may be adapted to reduce fluid egress, e.g., to reduce the likelihood of damage to the switch "S" due to fluid egress. In some embodiments, flange 45 is configured to facilitate positioning of the first user-accessible contact area 4b relative to the first aperture 71 and positioning of the second user-accessible contact area 4a relative to the second aperture 74.

As shown in FIG. 3, connector portion 30 defines a first axis "$A_1$-$A_1$" along the longitudinal direction of the connector portion 30, and a transverse or second axis "$A_2$-$A_2$" perpendicular thereto. Post body 32 defines a third axis "$A_3$-$A_3$" along the longitudinal direction of the post body 32, wherein the third axis "$A_3$-$A_3$" is at least substantially parallel to the second axis "$A_2$-$A_2$". Button "B" is selectively actuatable by depression of one or both of the contact areas 4a, 4b to cause movement of the post body 32 relative to the second axis "$A_2$-$A_2$", which, in turn, allows selective activation of the switch "S".

In some embodiments, switch assembly 100 is adapted to preclude activation of the switch "S" if the applied force to one or both of the contact areas 4a, 4b does not result in deflection of the third axis "$A_3$-$A_3$" by at least a predetermined angle (e.g., relative to the second axis "$A_2$-$A_2$"), e.g., to avoid or reduce unintended activation of the switch "S". In some embodiments, when user-applied force to one or both of the contact areas 4a, 4b causes movement of the first connector portion 31 resulting in deflection of the third axis "$A_3$-$A_3$" by at least a predetermined angle (e.g., relative to the second axis "$A_2$-$A_2$"), the resultant movement of the second connector portion 33 results in activation of the switch "S".

Hereinafter, methods of manufacturing a clip-over disposable assembly in accordance with the present disclosure are described with reference to FIGS. 5 and 6. It is to be understood that the steps of the methods provided herein may be performed in combination and in a different order than presented herein without departing from the scope of the disclosure.

Figure 5:
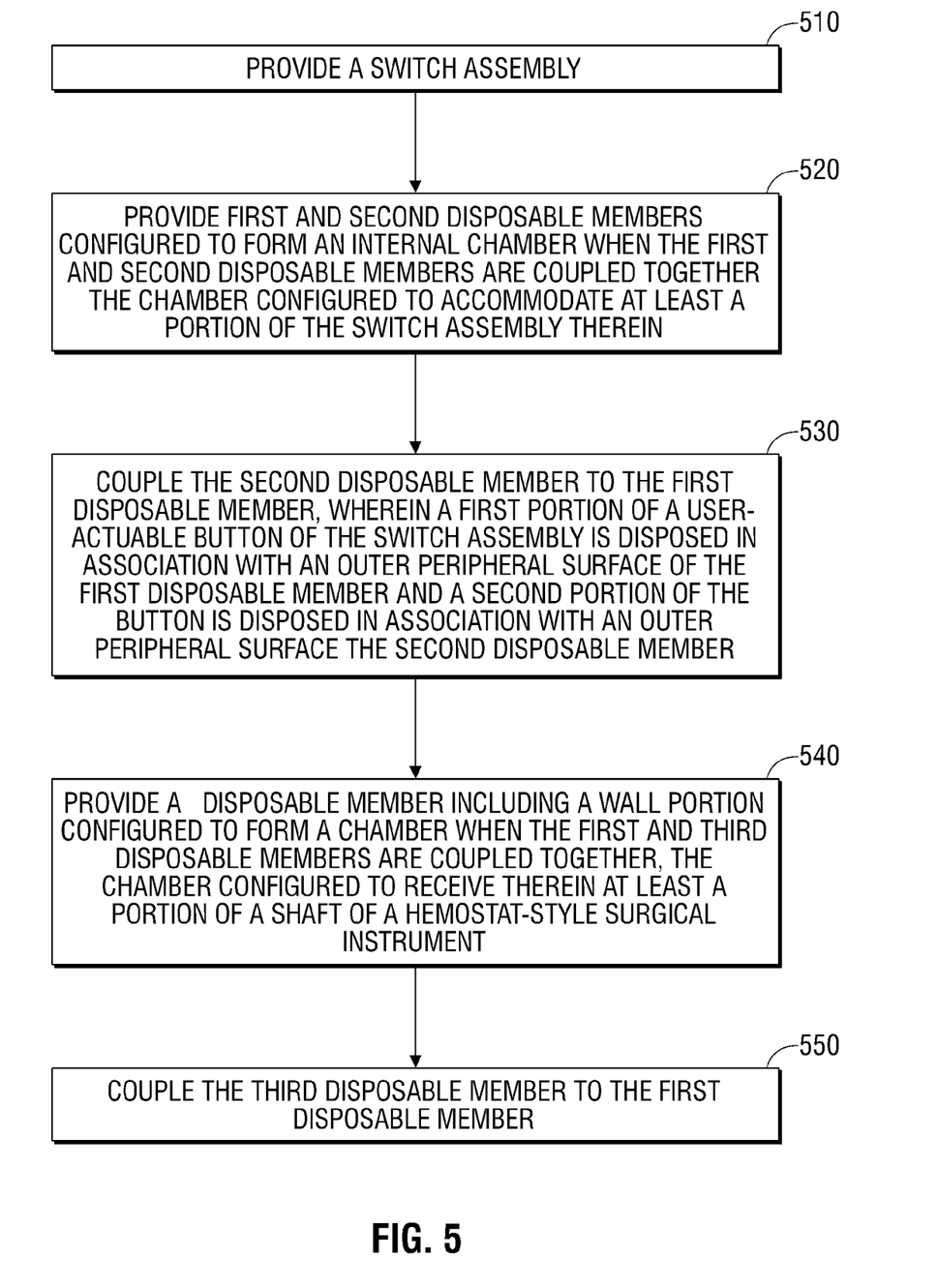
FIG. 5 is a flowchart illustrating a method of manufacturing a clip-over disposable assembly in accordance with an embodiment of the present disclosure.

FIG. 5 is a flowchart illustrating a method of manufacturing a clip-over disposable assembly 50 according to an embodiment of the present disclosure. In step 510, a switch assembly 100 is provided. Switch assembly 100 includes a user-actuatable button "B" including two user-accessible contact areas 4a and 4b.

In step 520, first and second disposable members 57, 58 are provided. The first and second disposable members 57, 58 are configured to form an internal chamber 76, 78 when coupled together. The chamber 76, 78 is configured to accommodate at least a portion 46, 48 of the switch assembly 100 therein. The first and second disposable members 57, 58 may be formed in whole or in part of any suitable electrically non-conductive material, e.g., a suitable polymeric or ceramic material.

In step 530, the second disposable member 58 is coupled to the first disposable member 57, wherein a first portion 4b of the user-actuatable button "B" is disposed in association with an outer peripheral surface of the first disposable member 57 and a second portion 4a of the user-actuatable button "B" is disposed in association with an outer peripheral surface the second disposable member 58. Any suitable joining method, e.g., ultrasonic welding, may be used to couple the second disposable member 58 to the first disposable member 57.

In step 540, a third disposable member 59 is provided. Third disposable member 59 includes a wall portion 55 configured to form a chamber "C" when the first and third disposable members 57, 59 are coupled together. The chamber "C" is configured to receive therein at least a portion of a shaft 14 of a hemostat-style surgical instrument 20.

In step 550, the third disposable member 59 is coupled to the first disposable member 57. In some embodiments, one or more conductors (e.g., three conductors 61a, 61b, 61c) suitable for transmitting electrosurgical energy through respective feed paths to end effectors 22 and 24 of an instrument 20 and/or electrical signals to control delivery of electrosurgical energy and/or feedback signals to control a source of electrosurgical energy 28 are over-molded prior to coupling the third disposable member 59 to the first disposable member 57, in step 550.

Figure 6:
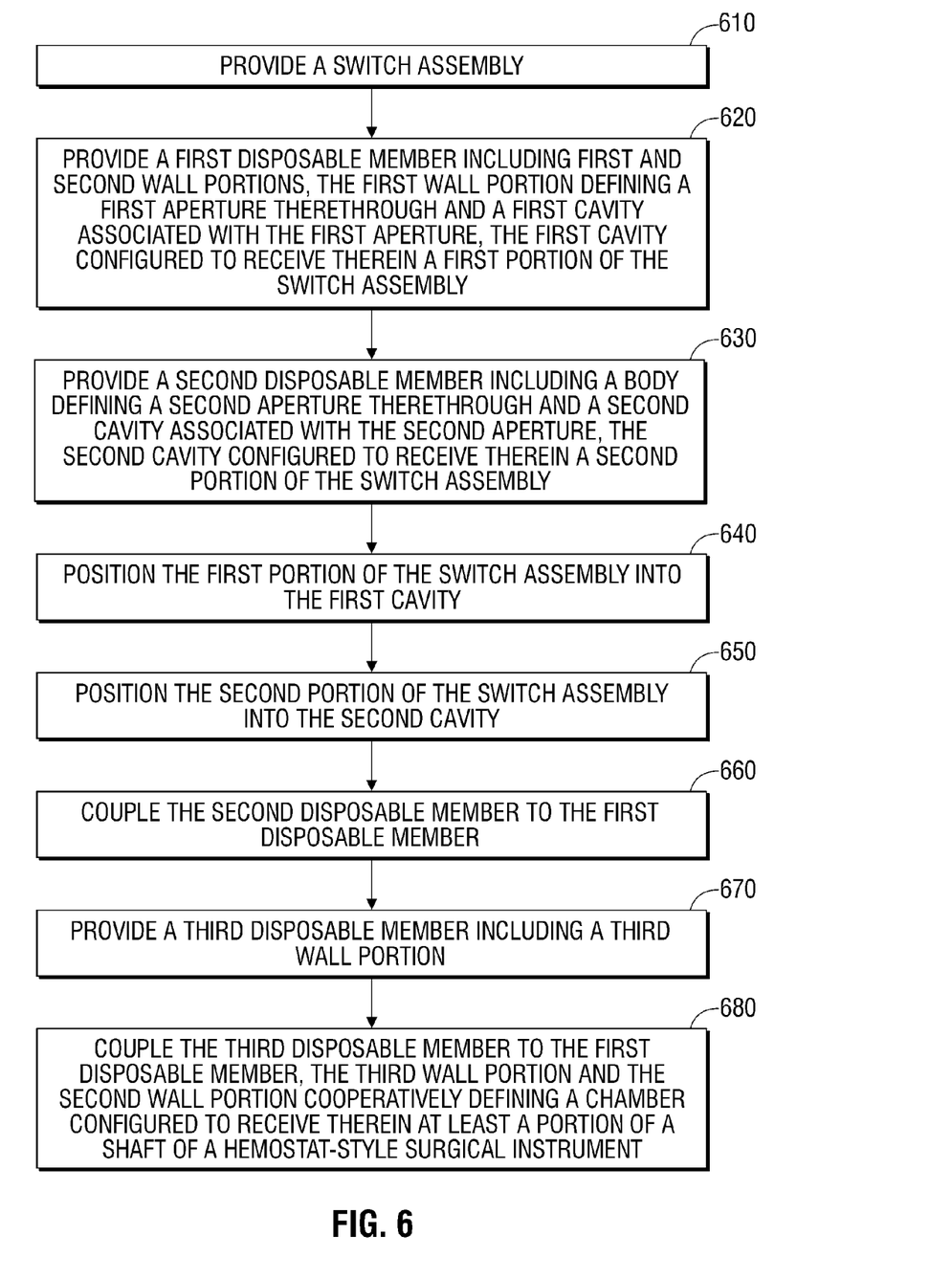
FIG. 6 is a flowchart illustrating a method of manufacturing a clip-over disposable assembly in accordance with another embodiment of the present disclosure.

FIG. 6 is a flowchart illustrating a method of manufacturing a clip-over disposable assembly 50 according to an embodiment of the present disclosure. In step 610, a switch assembly 100 is provided.

Switch assembly 100 includes a user-actuatable button "B" including first and second user-accessible contact areas 4a and 4b. In some embodiments, the switch assembly 100 also includes a post member 30 including a post body 32, wherein the post body 32 defines a longitudinal axis "$A_3$-$A_3$" transverse to the longitudinal axis "$A_1$-$A_1$" of the connector member 30. In some embodiments, the post body 32 bisects or otherwise divides the connector member 30 into a first connector portion 31 and a second connector portion 33.

In step 620, a first disposable member 57 is provided. First disposable member 57 includes first and second wall portions 51 and 52, respectively. The first wall portion 51 defines a first aperture 71 therethrough and a first cavity 76 associated with the first aperture 71. The first cavity 76 is configured to receive therein a first portion 46 of the switch assembly 100.

In step 630, a second disposable member 58 is provided. Second disposable member 58 includes a body 54 defining a second aperture 74 therethrough and a second cavity 78 associated with the second aperture 74. The second cavity 78 is configured to receive therein a second portion 48 of the switch assembly 100.

In step 640, the first portion 46 of the switch assembly 100 is positioned into the first cavity 76. The first user-accessible contact area 4b may be disposed in association with the first aperture 71.

In step 650, a second portion 48 of the switch assembly 100 is positioned into the second cavity 78. The second user-accessible contact area 4b may be disposed in association with the second aperture 74.

In step 660, the second disposable member 58 is coupled to the first disposable member 57. Any suitable joining method, e.g., ultrasonic welding, may be used to couple the second disposable member 58 to the first disposable member 57.

In step 670, a third disposable member 59 is provided. Third disposable member 59 includes a third wall portion 55.

In step 680, the third disposable member 59 is coupled to the first disposable member 57, wherein the third wall portion 55 and the second wall portion 52 cooperatively define a chamber "C" configured to receive therein at least a portion of a shaft 14 of a hemostat-style surgical instrument 20.

The above-described clip-over disposable assembly embodiments including a switch assembly and a disposable body configured for side-mounting onto a hemostat-style surgical instrument are suitable for use with various types of hemostat-style surgical instruments, such as without limitation, electrosurgical forceps, and may be suitable for a variety of uses and applications. Embodiments may be used in conjunction with electrosurgical devices suitable for use with open and/or laparoscopic surgical procedures.

The above-described methods of manufacturing a clip-over disposable assembly may be used in conjunction with a variety of electrosurgical devices adapted for treating tissue, such as bipolar electrosurgical forceps, monopolar electrosurgical forceps, and other hemostat-style surgical instruments. The above-described methods designed for ease of assembly a clip-over disposable assembly including a switch assembly and a disposable body configured for side-mounting onto a hemostat-style surgical instrument are suitable for use with a variety of types of hemostat-style surgical instruments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument, comprising:
    a hemostat-style device, including:
        first and second shaft members each defining a proximal end and a distal end;
        first and second handle members disposed at the proximal ends of the respective first and second shaft members;
        first and second jaw members extending distally from the distal ends of the respective first and second shaft members; and
        a pivot interconnecting the first and second shaft members towards the distal ends thereof such that movement of the first and second handle members between an open position and a closed position moves the first and second jaw members between a spaced-apart position and an approximated position for grasping tissue therebetween; and
    a clip-over assembly, including:
        an elongated body including first and second side walls interconnected by a base wall so as to define a U-shaped configuration, the first and second side walls and the base wall cooperating to define a U-shaped chamber configured to receive the first shaft member of the hemostat-style device and releasably engage the first shaft member therein; and
        at least one actuator operably disposed on at least one of the first or second side walls of the elongated body and positioned such that, with the first shaft member releasably engaged within the elongated body, the first shaft member is disposed on one side of the at least one actuator and the second shaft member is disposed on a second, opposite side of the at least one actuator.

2. The surgical instrument according to claim 1, wherein the at least one actuator includes first and second actuators operably disposed on the respective first and second side walls of the elongated body of the clip-over assembly.

3. The surgical instrument according to claim 1, wherein at least a portion of each of the first and second shaft members is formed from an electrically-conductive material.

4. The surgical instrument according to claim 3, wherein the elongated body of the clip-over assembly is formed from an electrically-insulative material.

5. The surgical instrument according to claim 1, wherein the elongated body of the clip-over assembly includes a proximal portion having the at least one actuator operably disposed thereon and an elongated distal portion extending distally from the proximal portion.

6. The surgical instrument according to claim 5, wherein, when the elongated body of the clip-over assembly is engaged about the first shaft member, at least a portion of the second shaft member is disposed between the first and second side walls of the elongated distal portion of the elongated body.

7. The surgical instrument according to claim 1, wherein the elongated body of the clip-over assembly is formed via injection molding.

8. The surgical instrument according to claim 1, wherein the at least one actuator includes an electrical switch.

9. The surgical instrument according to claim 8, wherein, when the elongated body of the clip-over assembly is engaged about the first shaft member, the electrical switch is selectively actuatable to supply energy to at least one of the first and second jaw members.

10. The surgical instrument according to claim 1, wherein the at least one actuator includes a joystick.

* * * * *